Aug. 27, 1963 W. F. KITTLE Plant Pat. 2,275
CLIMBING ROSE PLANT
Filed Jan. 23, 1962
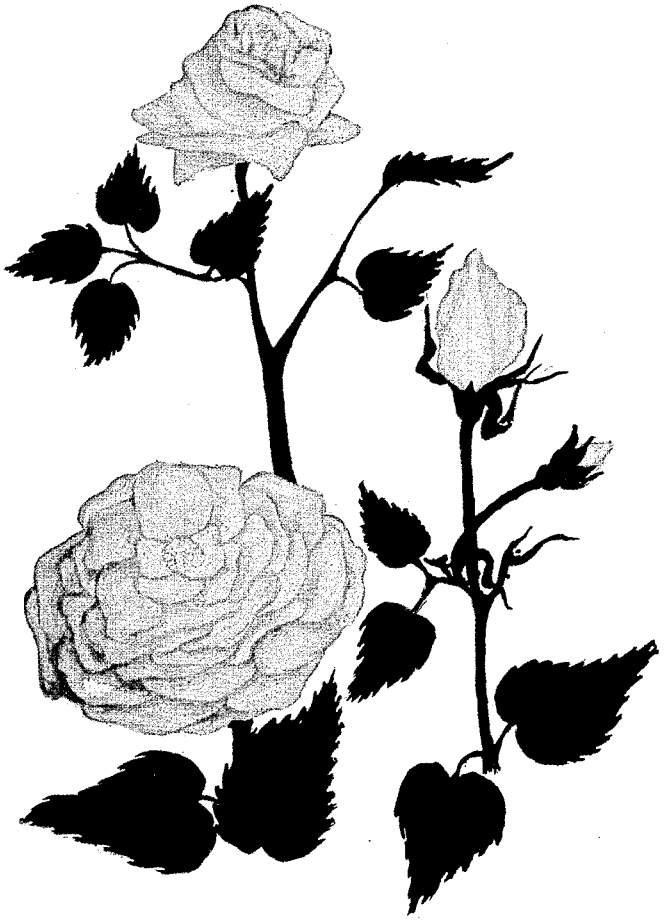
INVENTOR.
WILFRED F. KITTLE
BY
Leo J. Ma Lossi.
his ATTORNEY United States Patent Office Plant Pat. 2,275
Patented Aug. 27, 1963

2,275
CLIMBING ROSE PLANT

Wilfred F. Kittle, Pittsburgh, Pa., assignor to Lincoln Nursery Company, Penn Hill, Pa., a partnership Filed Jan. 23, 1962, Ser. No. 168,292
1 Claim. (Cl. Plt.—5)

The present invention relates to a new and distinct variety of climbing rose plant of the hybrid tea class, which was accidentally produced as the result of budding a Star of Holland (unpatented hybrid tea rose) to *Rosa multiflora* understock.

As a result of this budding of the two plants as stated above, an unusual condition was produced. As would be expected, a Star of Holland rose plant grew from the understock of the *Rosa multiflora*. However, in addition, at the point of juncture of these two varieties, a separate bud grew. The original budding was located on the understock about two inches (2") underground. The Star of Holland rose plant had grown and blossomed before applicant was aware of the presence of the separate bud, which blossomed about two to three months after the budding and developed leaves, but was thornless with a large flower of pink color and marked fragrance. The Star of Holland cane had grown upward at a substantial angle to the understock while the growth from the separate bud grew almost straight up. When discovered, this growth from the separate bud was about six inches (6") long, heavy, succulent and reddish in color. Thus, from a routine budding intended to raise a Star of Holland rose plant, the bud union produced a wholly different rose plant; namely, a thornless climber bearing 3 to 5 large fragrant blooms on new growth.

Thus, this new variety possesses the following unique combination of characteristics which are outstanding and which distinguish it favorably from its parent, as well as from all other varieties of which I am aware:

(1) New leaves are reddish turning to green as the leaves mature;

(2) The flower stems are 6–8 inches long; are sturdy and are easily capable of carrying 3–5 flowers in an upright position;

(3) The buds are firm, well-shaped and pointed and of medium size;

(4) The flowers produced are large, double flowers having imbricated petals with the outer petals thereof rolling outwardly and downwardly, and having a fragrance characterized by a slight musk odor like the old June shrub rose;

(5) The color of the flower is a distinctive deep uniform pink which lightens progressively toward the calyx;

(6) The stems are sturdy, arching and are greenish-red in color; and (7) The entire plant is completely free of sharp pointed thorns, there occurring only a slight roughening at the underside of the matured rachis at the point of juncture of the leaves.

In comparison with the Star of Holland, the present plant is free of sharp pointed thorns having only the slight roughening referred to in (7) above. Also, the color of the flower produced differs in that the new variety has greater doubleness of petal production therein and has a distinctive deep uniform pink coloration in the individual petal graduating to a light pinkish hue at the base thereof. Also, the present bud sport is hardier than the Star of Holland plant, having successfully survived temperatures of −20° F. without serious damage thereto. In a particular instance, one of this new variety of plant having a height of about 6 feet had about 8 inches of the tips of the canes frozen as a result of exposure to these severe weather conditions, but the rest of the plant showed no injury and suffered no ill effects.

Asexual reproduction of this new variety by rooted cuttings was performed in Penn Hills, Pennsylvania, a location several miles east of Pittsburgh, Pennsylvania, showing that the aforementioned characteristics and distinctions come true to form and are established and transmitted through successive propagations.

The accompanying drawing shows typical specimens of the vegetative growth and flowers of this new variety in different stages of development with the growth and flowers depicted in color as nearly true as is reasonably possible to produce them in a color illustration of this character.

The following is a detailed description of this new variety with color terminology in accordance with the Dictionary of Color by Maerz and Paul (published by McGraw-Hill Book Co. Inc., 1st edition, 1930), except where general color terms of ordinary dictionary significance are obviously applicable.

*Flower*

Locality where grown and observed: Penn Hills, Pennsylvania.

Flowers borne: 3–5 flowers on strong, short stems.

Quantity of bloom: In the spring and fall, outdoor plants are almost covered with blooms; throughout the summer, without cutting back for new growth, there will be about one dozen blooms per plant at all times.

Continuity: Intermittent.

Fragrance: Moderate and in the nature of the fragrance of the June shrub rose.

Bud:

*Peduncle.*—Of medium length and medium heavy structure, erect, stiff and entirely smooth; reddish green in color.

*Before calyx breaks.*—Size—medium. Form—short and pointed having foliaceous appendages on the surface of the bud. Color—reddish green.

*As calyx breaks.*—Color—light shade of pink.

*As first petal opens.*—Size—medium. Form—medium pointed. Color—deep pink.

Bud opens up well; opening is not retarded by adverse temperature or weather conditions.

Bloom:

*Size (when fully opened).* — Medium large being from 3 to 4 inches in diameter.

*Petalage.*—Very double; usually with no stamens showing and averaging from 20 to 40 petals, plus a few petaloids.

*Form.*—High-centered at first and remaining more or less high-centered; petals being very loosely rolled outward at first at apical margins and more rolled at maturity.

Petals:

*Texture.*—Soft and of medium thickness. Inside—shiny-satiny. Outside—satiny.

*Shape.*—The individual petals are about as broad as they are long, the side edges of the petal diverging from the zone of attachment of the petal and the outermost rim of the petal being arcuate; entire.

The general color effect on newly-opened blooms and that on blooms opened for several days is about the same. The petals drop off cleanly after about the fifth day after the opening of the bud in an outside garden in the month of June. This is a description of a newly opened flower:

*Color.*—The typical petal begins at the tip as Martius Y, Plate 9–J1. This color then slowly fades into Marguerite Y, Plate 10–C1 and then to Oyster White+, Plate 10–B1. This then disperses into Thulite Pink, Plate 50–I1 which finally varies to the color of Plate 50–L7.

*Reproductive Organs*

Stamens: From medium in number to many; arranged irregularly about pistils.
Filaments: From short to medium in length; most having anthers.
Anthers: All are open at once; more or less. Color—dull yellow.
Pollen: Moderate in abundance. Color—yellow.
Pistils: Medium in quantity.
Ovaries: Undeveloped in the flowers observed to date.
Hips: Elongated and globular in form; smooth.
Sepals: Permanent; medium length; curved downwardly.
Seeds: None produced to date.

*Plant*

Foliage:

*Leaves.*—Compound of 3 to 5 leaflets; normal quantity; large; leathery and dull green.

*Leaflets.*—Shape—oval, with acute apex. Base—rounded. Margin—simply serrate.

*Color.*—New leaf—Aubusson, Plate 7–5H around the edges with the balance thereof Hellebore Green, Plate 23–3L. Mature Leaf—Art Green, Plate 22–7L.

*Rachis.*—Upper side—grooved; sparsely glandular. Under side—smooth, except for occasional roughness after maturity at the juncture of the leaflets.

Growth:

*Habit.*—Vigorous, upright, arching.

*Growth.*—Free.

*Canes.*—Heavy.

*Main stems.*—Color—reddish green and free of prickles or thorns.

*Branches.*—Color—reddish green and free of prickles or thorns.

*New shoots.*—Color—greenish red.

I claim:

A new and distinct variety of climbing rose plant of the hybrid tea class, substantially as herein shown and described, characterized particularly as to novelty by the unique combination of large double flowers having imbricated petals and a pronounced June shrub rose fragrance and a distinctive rich pink general color tonality and heavy canes; main stems, branches and rachis completely free of pointed prickles.

No references cited.